(12) United States Patent
Cristina Araújo Vieira et al.

(10) Patent No.: US 10,576,042 B2
(45) Date of Patent: Mar. 3, 2020

(54) COMPOSITION COMPRISING POLYELECTROLYTE COMPLEXES, METHODS AND USES THEREOF

(71) Applicant: ASSOCIATION FOR THE ADVANCEMENT OF TISSUE ENGINEERING CELL BASED TECHNOLOGIES & THERAPIES ASSOCIACAO, Braga (PT)

(72) Inventors: Silvia Cristina Araújo Vieira, Braga (PT); Joaquim Miguel Antunes De Oliveira, Braga (PT); Rui Luís Gonçalves Dos Reis, Oporto (PT); Joana Catarina Da Silva Correia, Braga (PT)

(73) Assignee: ASSOCIATION FOR THE ADVANCEMENT OF TISSUE ENGINEERING CELL BASED TECHNOLOGIES & THERAPIES ASSOCIAÇAO, Braga (PT)

( * ) Notice: Subject to any disclaimer, the term of this patent is extended or adjusted under 35 U.S.C. 154(b) by 0 days.

(21) Appl. No.: 15/778,380

(22) PCT Filed: Nov. 23, 2016

(86) PCT No.: PCT/IB2016/057077
§ 371 (c)(1),
(2) Date: May 23, 2018

(87) PCT Pub. No.: WO2017/089974
PCT Pub. Date: Jun. 1, 2017

(65) Prior Publication Data
US 2018/0344652 A1  Dec. 6, 2018

(30) Foreign Application Priority Data
Nov. 23, 2015 (PT) .......................... 108974

(51) Int. Cl.
| | |
|---|---|
| A61K 36/00 | (2006.01) |
| A61K 9/50 | (2006.01) |
| A61K 9/00 | (2006.01) |
| A61P 1/18 | (2006.01) |
| A61P 3/04 | (2006.01) |
| A61P 3/10 | (2006.01) |
| A61P 15/08 | (2006.01) |
| A61P 35/00 | (2006.01) |
| A61K 9/48 | (2006.01) |
| A61K 35/39 | (2015.01) |
| A61K 35/52 | (2015.01) |

(52) U.S. Cl.
CPC .......... *A61K 9/5036* (2013.01); *A61K 9/0019* (2013.01); *A61K 9/4858* (2013.01); *A61K 9/5052* (2013.01); *A61K 35/39* (2013.01); *A61K 35/52* (2013.01); *A61P 1/18* (2018.01); *A61P 3/04* (2018.01); *A61P 3/10* (2018.01); *A61P 15/08* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 5,334,640 A | 8/1994 | Desai et al. | |
| 6,726,934 B1 | 4/2004 | Prokop | |
| 9,005,662 B2 | 4/2015 | Schlenoff | |
| 2012/0076854 A1* | 3/2012 | Hope | A61K 9/19 424/451 |

FOREIGN PATENT DOCUMENTS

| | | |
|---|---|---|
| WO | WO 2000/001373 | 1/2000 |
| WO | WO 2004/032881 | 4/2004 |
| WO | WO 2013/133705 | 9/2013 |

OTHER PUBLICATIONS

Yamamoto et al, Polyion complex fiber and capsule formed by self-assembly of poly-L-lysine and gellan at solution interfaces. Journal of Applied Polymer Science (2000), vol. Date 2001, 79(3), 437-446 (Year: 2000).*

Yamamoto, Hiroyuki, et al. "Polyion complex fiber and capsule formed by self-assembly of poly-L-Lysine and gellan at solution interfaces." *Journal of applied polymer science* 79.3 (2001): 437-446.

* cited by examiner

*Primary Examiner* — Qiuwen Mi
(74) *Attorney, Agent, or Firm* — Leason Ellis LLP (57) ABSTRACT

The present disclosure relates to a composition of at least one predominantly positively charged polyelectrolyte polymer and at least one predominantly negatively charged polyelectrolyte polymer, a preferred composition comprises poly-L-lysine and a gellan gum, preferably a methacrylate gellan gum. The present subject-matter further relates to methods for generating composition of the present disclosure and to uses of a mixture according to the disclosure for biomedical applications such as cellular and acellular systems for tissue engineering and regenerative medicine applications or as drug delivery systems, for the treatment of several diseases namely diabetes mellitus.

19 Claims, 9 Drawing Sheets

COMPOSITION COMPRISING POLYELECTROLYTE COMPLEXES, METHODS AND USES THEREOF

CROSS-REFERENCE TO RELATED PATENT APPLICATIONS

This is a U.S. National Phase Application under 35 U.S.C. § 371 of International Patent Application No. PCT/IB2016/057077, filed Nov. 23, 2016, and claims priority to Portuguese Patent Application No. 108974 filed Nov. 23, 2015, which is incorporated by reference in its entirety. The International Application was published on Jun. 1, 2017, as International Publication No. WO 2017/089974 A1.

TECHNICAL FIELD

The present disclosure relates to a composition of at least one predominantly positively charged polyelectrolyte polymer and at least one predominantly negatively charged polyelectrolyte polymer, a preferred composition comprises poly-L-lysine and a gellan gum (GG), preferably a methacrylate gellan gum (GG-MA).

The present subject-matter further relates to methods for generating composition of the present disclosure and to uses of a mixture according to the disclosure for biomedical applications such as cellular and acellular systems for tissue engineering and regenerative medicine applications or as drug delivery systems (DDS), for the treatment of several diseases namely diabetes mellitus.

BACKGROUND

Polyelectrolyte complexes (PEC) are produced by the interfacial complexation of polyelectrolytes. This process is mainly driven by the electrostatic bonds formed between the two oppositely charged polyelectrolytes. One of the great advantages of this process is its compatibility with mild conditions, namely room temperature, aqueous environment and physiological pH, and its non-deleterious effect on cells or drugs. Thence, cells, drugs, small peptides and others can easily be incorporated in structures produced by polyelectrolyte complexation without compromising their viability and bioactivity. PEC shape and size is easily adjustable (e.g. capsules (3D), fibers, membranes (2D), sacs (with an aperture), and microbioreactors) making possible their use on a plethora of biomedical applications. On a tissue engineering perspective, the possibility to include different components—as cells and drugs—into very specific structures is attractive, thus composing a multicomponent system. PEC can then be used alone as scaffolds or in combination with hydrogels as a way to enhance their mechanical properties.

Gellan gum is a linear anionic heteropolysaccharide secreted by the bacteria *Sphingomonas elodea*. Its molecular structure is based in one repeating unit consisting of glucose-glucuronic acid-glucose-rhamnose. In the native form, or high acyl form, two types of acyl substituents are present: acetyl and L-glyceryl. Low acyl gellan gum is obtained through alkaline hydrolysis of native gellan gum, which removes both of the acyl residues. Both forms of gellan gum form hydrogels in presence of metallic ions, and upon temperature decrease.

It is acid and heat resistant and has a free carboxylic group per repeating unit, which can be used for improvement of functionalization. Moreover, the presence of this carboxylic group confers to gellan gum a negative charge at neutral pH ($pKa=3.1$). Thus, gellan gum can be combined with positively charged polymers in order to prepare PEC systems.

Poly-L-lysine is a lysine homopolymer. Therefore, it results from the polymerization of a lysine aminoacid. Since lysines have two different amines, polymerization process can start either from the amine located at ε-carbon (ε-polylysine) or from the amine located at the α-carbon (α-polylysine), which applies to poly-L-lysine. Due to the presence of a positively charged hydrophilic amino group, poly-L-lysine is positively charged at physiological pH.

Several patent documents are based on the application of PEC for different purposes, including cell encapsulation.

U.S. Pat. No. 5,334,640 refers to crosslinked biocompatible compositions comprising an ionically crosslinked component and a covalently crosslinked component for encapsulating biologic compounds. Crosslinkable mixtures and method are also disclosed.

Document WO 2013133705 A1 relates to a composition comprising a polyelectrolyte complex, and comprising at least one biocide. A preferred composition comprises lignosulfonate and chitosan. The document further relates to methods for generating a composition and to uses of a mixture for protecting an agricultural plant or plant part against a pathogen.

U.S. Pat. No. 9,005,662 B2 describes a polyelectrolyte complex comprising an interpenetrating network. The polyelectrolyte complex further comprises a plurality of closed-shell pores, having at least one average transverse dimension between about 100 nanometers and about 1000 micrometers.

Document WO 2000001373 A1 defines a method for encapsulating a core material within a capsule having a permeable or semipermeable membrane. A complex formation reaction between oppositely charged polymers is used wherein one of the polymers is an oligosaccharide such as chitosan and the reaction is carried out at a pH between about 6.6 and 7.5.

Document WO 2004032881 A3 relates to compositions for treating a disease by implanting encapsulated biological material into a patient. The components of the used coatings can include natural and synthetic polymers, macromers, accelerants, co-catalysts, photo-initiators, and radiation and can be manipulated on order to obtain different degrees of biocompatibility, protein diffusivity characteristics, strength, and biodegradability.

These facts are disclosed in order to illustrate the technical problem addressed by the present disclosure.

General Description

The present disclosure provides a PEC systems based on gellan gum and poly-L-lysine. These systems may be processed with different architectures, including capsules, micro- and nanofibers, membranes, sacs with inner micro-nanofibers or hydrogels, and microbioreactors, and it is useful for tissue engineering and regenerative medicine applications, as well as for drug delivery.

Taking advantage of self-assembly processes, as the aforementioned PEC, it is possible to develop stable materials with specific tailored design. As they are oppositely charged, in particular gellan gum and poly-L-lysine can be used as platform to obtain self-assembly PEC systems.

Herein, it is disclosed the use of a gellan gum-based polyelectrolyte complex that can be applied for cell encapsulation purposes. Although a number of hydrogel systems based in natural polymers (e.g., alginate and chitosan) have been developed to tackle cell encapsulation, they still present several problems such as variability of production, poor nutrient supply, insufficient mechanical properties or desired stability and tuned permeability to cells. Using the aforesaid PEC, it is possible to construct a thin membrane with adjusted permeability that surrounds a biocompatible core, preferably liquefied. This membrane allows the inflow of essential nutrients and oxygen and outflow of cell waste and metabolites while blocking the recognition by immune cells. This immunoprotective device permits cell transplantation-based therapies without the using of deleterious immunosuppression drugs.

One aspect of the present subject-matter discloses a composition for use in veterinary or in human medicine comprising a polyelectrolyte complex comprising a cationic polymer, poly-L-lysine, and a gellan gum.

In one embodiment for better results, the polyelectrolyte complex material of the present subject-matter may comprises a gellan gum and a poly-L-lysine. In particular suitable for tissue engineering and regenerative medicine applications or as drug delivery systems.

In one embodiment for better results, the composition of the present subject-matter may comprise 0.05-1% (w/v) of poly-L-lysine, 0.5-10% (w/v) of gellan gum.

In other embodiment for better results, the composition of the present subject-matter may comprise 0.05-0.1% (w/v) of poly-L-lysine, 0.5-3% (w/v) of gellan gum. Preferably 0.5-1.5% (w/v) of gellan gum; more preferably, 0.5-1.5% w/v of low acyl GG.

In other embodiment for better results the gellan gum may be a low-acyl gellan gum, a high-acyl gellan gum, a methacrylated gellan gum, and combinations thereof.

In another embodiment for better results the gellan gum acylation degree may be from no acyl groups up to two acyl substituents—acetate and glycerate—both located on the same glucose residue.

In another embodiment for better results the gellan gum acylation degree may be one glycerate per repeat and one acetate per every two repeats.

In another embodiment for better results the methacrylated gellan gum may comprises a methacrylation degree up to 10%, preferably between 0.5-5%, more preferably 1-3%, even more preferably 1-1.5%. Formulations of gellan gum with different degrees of acylation (from low to high) and poly-L-lysine serve as precursor materials. When in contact, these materials interact and form a stable polyelectrolyte complex material with tunable shape and size. The material can be then tailored to form capsules to withstand the encapsulation of human and animal cells and/or drugs; fibres; 3D structures or scaffolds; micro- or nanoparticles; and any combination thereof.

In other embodiment for better results the gellan gum molecular weight may be between $5\text{-}10 \times 10^4$ Da (methacrylated), $2\text{-}3 \times 10^5$ Da (low acyl) and $1\text{-}2 \times 10^6$ Da (high acyl).

In another embodiment for better results the poly-L-lysine molecular weight may be between 30-500 kDa, preferably between 70-300 kDa. By varying the molecular weight of gellan gum and poly-L-lysine it is possible to adjust both biological and physicochemical properties (such as strength, flexibility, softness, degradability, chemical resistance and permeability) of the polyelectrolyte complex material, to meet specific needs.

In another embodiment for better results the composition of the present disclosure may further comprise an anti-inflammatory agent, an antiseptic agent, an antipyretic agent, an anaesthetic agent, a therapeutic agent, a biological cell, a biological tissue and combinations thereof. Preferably, may comprise an animal or human cell, or stem cell, or combinations thereof. More preferably, may comprise an animal or human pancreatic β-cell.

In another embodiment for better results the composition may further comprise a plurality of hydrogels. More preferably, the second, or more hydrogels, is selected from a list consisting of carbopol, Matrigel®, hyaluronic acid, carboxymethylchitosan, dextran, alginate, collagen, and mixtures thereof.

In another embodiment for better results the composition may further comprise a coupling agent, in particular the coupling agent may be selected from the group consisting of 4-(4,6-dimethoxy-1,3,5-triazin-2-yl)-4-methylmorpholinium chloride, glutaraldehyde, epichlorohydrin, dianhydrides, diamines, and mixtures thereof.

Another aspect of the present invention relates with the use of the composition of the present subject-matter in the treatment of diseases that involve the repair or regeneration of tissues; or the use as a drug delivery system; or use in cell therapy or advanced-therapy medicinal product.

Another aspect of the present invention relates with the use of the composition of the present subject-matter in the treatment or prevention of diabetes; in particular for the treatment of type 1 diabetes mellitus, type 2 diabetes mellitus, or gestational diabetes; or obesity, ageing related-diseases, tumours or pancreatic diseases.

Another aspect of the present invention relates to the use of the composition of the present subject-matter in the treatment or prevention of female infertility, in particular the use of the sac/membranes/capsules for ovarian protection, or for ovarian follicle protection or for ovocyte protection.

Another aspect of the present invention relates to capsule, sac, fibre, membrane, or microbioreactors comprising the compositions of the present subject-matter.

In another embodiment the external size of the capsules may be less than 20 mm, in particular up to 3 mm.

In another embodiment the sacs may comprise inner fibres, or hydrogel, or combinations thereof. In particular, the inner fibres are microfibres, or nanofibres or combinations thereof.

Throughout the description and claims the word "comprise" and variations of the word, are not intended to exclude other technical features, additives, components, or steps. Additional objects, advantages and features of the disclosure will become apparent to those skilled in the art upon examination of the description or may be learned by practice of the disclosure. The following examples and drawings are provided by way of illustration, and they are not intended to be limiting of the present disclosure. Furthermore, the present disclosure covers all possible combinations of particular and preferred embodiments described herein.

BRIEF DESCRIPTION OF THE DRAWINGS

The following figures provide preferred embodiments for illustrating the description and should not be seen as limiting the scope of invention.

DETAILED DESCRIPTION

The present disclosure provides polyelectrolyte complexes in particular compositions comprising poly-L-lysine and gellan gum, their processing methods and use in the field of tissue engineering and regenerative medicine or drug delivery systems.

Gellan gum is an anionic heteropolysaccharide that form hydrogels in the presence of mono-, di-, and tri-valent ions and exists in two different forms, the high-acyl gellan gum and the low-acyl gellan gum. In high-acyl gellan gum, the acyl residues are located on the periphery of the helix, obstructing the polymer chain association, resulting in soft, elastic and non-brittle gels. In contrast, low-acyl gellan gum produces firm, non-elastic, brittle gels since ions can easily link polymer chains and form a branched network.

Poly-L-lysine is a cationic polymer, synthetically produced, commonly used as a charge enhancer and surface coating for adhesion purposes. It is available on formulations with different molecular weight that can vary from 30-70 kDa (lower molecular weight) to more than 300 kDa (high molecular weight).

Due to the anionic nature of gellan gum, it can be conjugated with other positively charged polymers, in particular poly-L-lysine, forming stable PEC systems.

PEC based on gellan gum and poly-L-lysine are formed by combination of the two compounds at controlled pH and temperature. By varying the components ratio, it was possible to obtain materials with different physicochemical properties. The materials are stable under physiological conditions due to the formed electrostatic bounds. The formation of PEC was verified by Fourier-transform Infrared (FTIR) analysis performed before and after PEC formation. The biological properties of the obtained material were assessed in vitro, and using different cell types and cell agglomerates (see embodiments of FIGS. 1 and 6).

The final physicochemical and biological properties, as well as the shape, of the PEC systems can be tailored by applying different formulations and processing conditions.

An aspect of the disclosure is to improve both the mechanical performance of gellan gum hydrogel capsules and their permeability to nutrients and cell metabolites. Formulations can use different gellan gum forms and types of poly-L-lysine, i.e. with different degrees of acylation and molecular weight that self-assemble into PEC as a result of their opposite charge. This process allows the production of capsules with tuned physical properties (e.g., strength, softness, flexibility, degradability and permeability to solutes, bioactive molecules and cells) according to the desired use. Along with having adaptable properties, these systems can also provide the advantage of being straightforward, with no need of other chelating agents for capsule formation, and under physiological-like conditions (37° C. and pH 7.4).

In an embodiment, the PEC systems of the present subject-matter used alone or together with cells and/or bioactive molecules, can provide a plethora of potential applications in tissue replacement and regenerative approaches, mostly for cell encapsulation technologies, namely pancreatic cells.

The description of this disclosure is complemented through the following examples that are intended to provide a better understanding of the same, although these examples should not be addressed with a restrictive nature.

Synthesis of PEC system as capsules—In an embodiment, the PEC capsules were prepared by reacting gellan gum with poly-L-lysine. Two commercially available gellan gum were used, namely: 1) low-acyl gellan gum (Sigma, St. Louis, Mo., USA) and 2) methacrylated gellan gum (Mimsys® G, Irisbiosciences, Portugal). For that, gellan gum solutions, with a final concentration varying from 0.5 to 3% (w/v), were prepared by dissolving the material in distilled water under constant stirring. For low-acyl gellan gum, the solutions were heated until 90° C. to obtain a homogenous dispersion. Then, solutions were cooled down 10° C. above the respective setting temperature.

In an embodiment, PEC capsules were produced as follows: the well-dispersed gellan gum solution was extruded drop-wise from a 30G needle into a poly-L-lysine bath (Mw from 30,000 to 300,000, Sigma, St. Louis, Mo., USA) using a peristaltic pump to control the flow rate. The formed capsules were maintained on poly-L-lysine solution to allow the formation of a complete PEC membrane, and then transferred to PBS (Phosphate-buffered saline).

Synthesis of PEC system as particles—In an embodiment, the PEC capsules were prepared by reacting gellan gum with poly-L-lysine. Two commercially available gellan gum were used, namely: 1) low-acyl gellan gum (Sigma, St. Louis, Mo., USA); and 2) methacrylated gellan gum (Mimsys® G, Irisbiosciences, Portugal). For that, gellan gum solutions, with a final concentration varying from 0.5 to 3% (w/v), were prepared by dissolving the material in distilled water under constant stirring. For low-acyl gellan gum, the solutions were heated until 90° C. to obtain a homogenous dispersion. Then, solutions were cooled down 10° C. above the respective setting temperature.

The well-dispersed gellan gum solution can be then extruded drop-wise from a 30G needle into a poly-L-lysine bath (Mw from 30,000 to 300,000, Sigma, St. Louis, Mo., USA) using a peristaltic pump to control the flow rate. The formed capsules were maintained on poly-L-lysine solution to allow the formation of a complete PEC membrane.

In an embodiment, to obtain particles, as-prepared capsules can be transferred into a 3% $CaCl_2$ bath to allow the ionic cross-linking of the inner hydrogel. At last, particles were immersed in PBS until further use.

PEC system with encapsulated cells—In an embodiment, the PEC capsules with encapsulated cells were prepared by reacting gellan gum with poly-L-lysine. Two commercially available gellan gum were used, namely: 1) low-acyl gellan gum (Sigma, St. Louis, Mo., USA); and 2) methacrylated gellan gum (Mimsys® G, Irisbiosciences, Portugal). For that, gellan gum solutions, with a final concentration varying from 0.5 to 3% (w/v), were prepared by dissolving the material in distilled water under constant stirring. For low-acyl gellan gum, the solutions were heated until 90° C. to obtain a homogenous dispersion. Then, solutions were cooled down 10° C. above the respective setting temperature.

In an embodiment, cells were carefully mixed with the different gellan gum suspensions and the mix was extruded drop-wise from a 30G needle into a poly-L-lysine bath (Mw from 30,000 to 300,000, Sigma, St. Louis, Mo., USA) using a peristaltic pump to form capsules. The formed capsules were maintained on poly-L-lysine solution for 10 minutes, to allow the formation of a complete membrane and the resulting PEC capsules with loaded cells.

In an embodiment, PEC capsules can be subsequently cultured together with the previously described growth medium and kept at 37° C. with 5% $CO_2$ in a standard tissue culture incubator.

Figure 1:
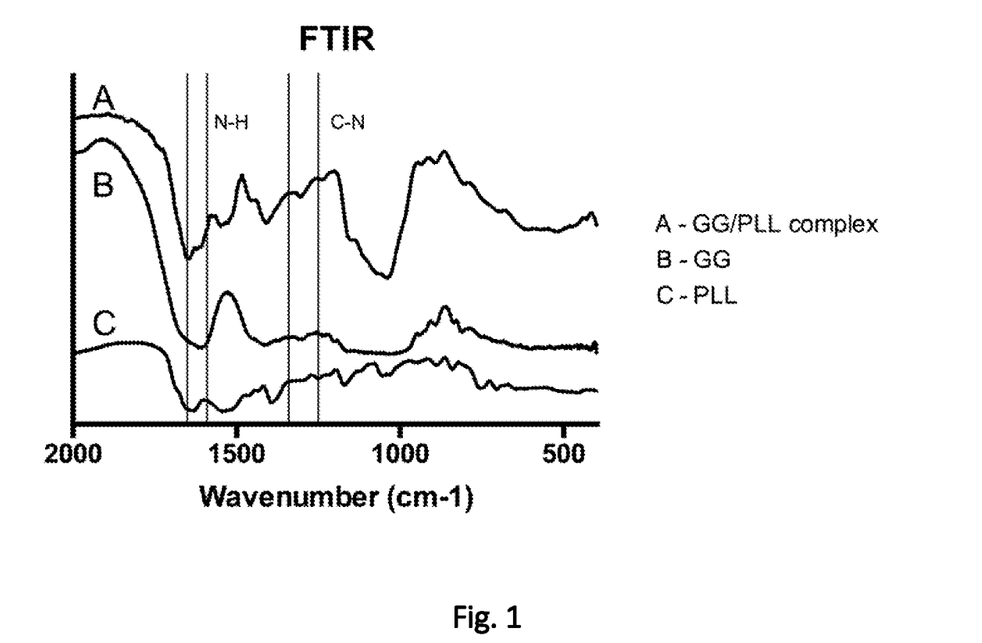
FIG. 1: Schematic representation of a FTIR spectra of (A) GG/PLL complex, (B) GG and (C) PLL.
Figure 2:
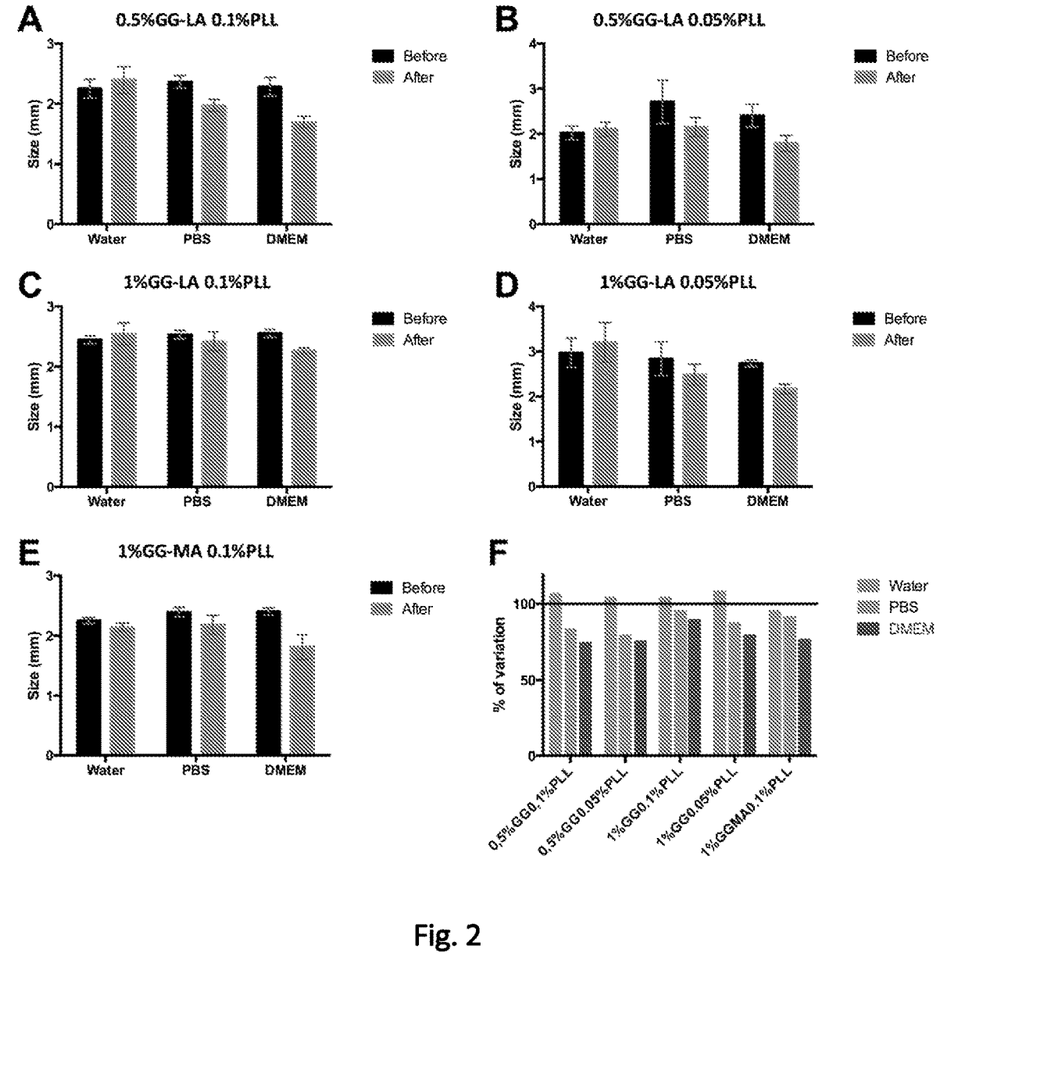
FIG. 2: Size comparison of capsules before (black) and after (grey) immersion in distilled water, PBS and DMEM. Different formulations were used to produce the capsules, namely: A—0.5% GG-LA 0.1% PLL; B—0.5% GG-LA 0.05% PLL; C—1% GG-LA 0.1% PLL; D—1% GG-LA 0.05% PLL; E—1% GG-MA 0.1% PLL; and F—Size variation after immersion in distilled water, PBS and DMEM as compared to capsules measured before incubation.

In an embodiment, the FTIR spectra of GG/PLL complex of the present disclosure, are present in FIG. 1 herein (a) is the FTIR spectra of GG/PLL complex of the present disclosure, (b) is the FTIR spectra of GG and (c) is the FTIR spectra of PLL.

An embodiment for measuring the size and morphology of Capsules—Capsules of the present disclosure were placed either in water, PBS (Phosphate-buffered saline) or DMEM (Dulbecco's Modified Eagle Medium) for 1 week. Particles size was measured before and after the environmental change.

Figure 3:
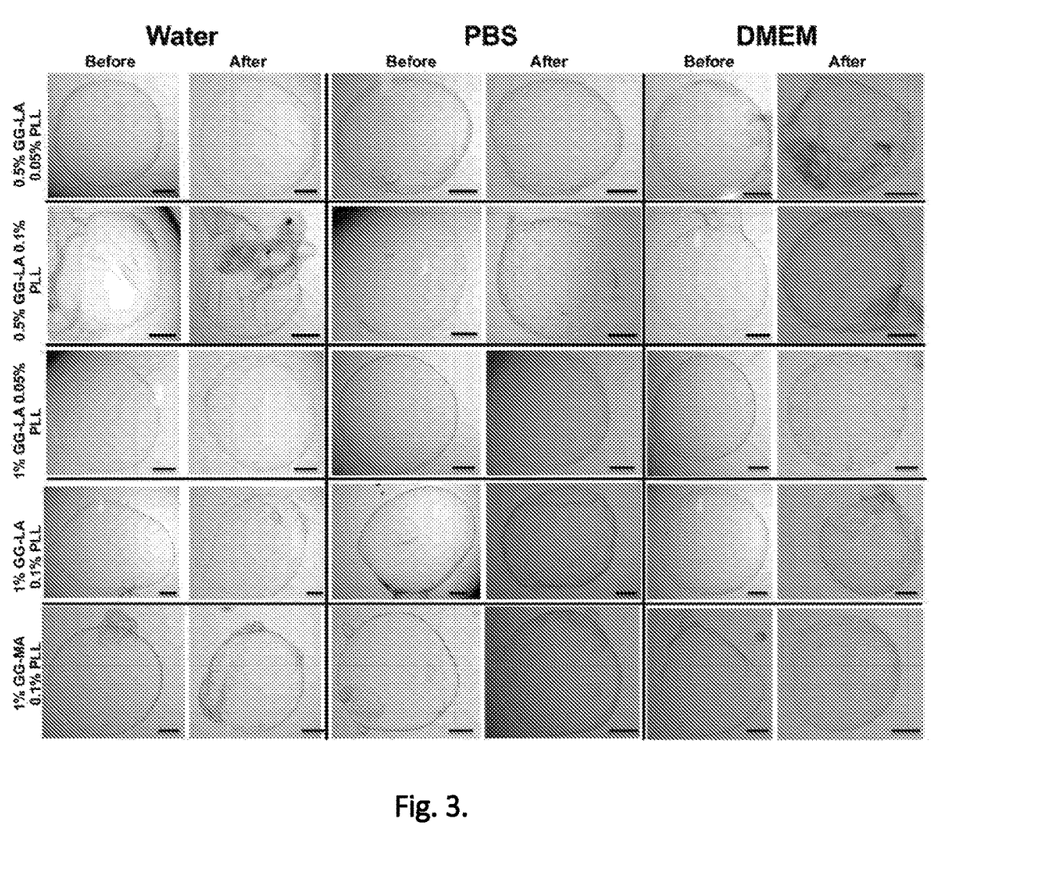
FIG. 3: Pictures of different formulations of GG/PLL capsules, before and after incubation with distilled water, PBS and DMEM. Scale bar=500 μm.
Figure 4:
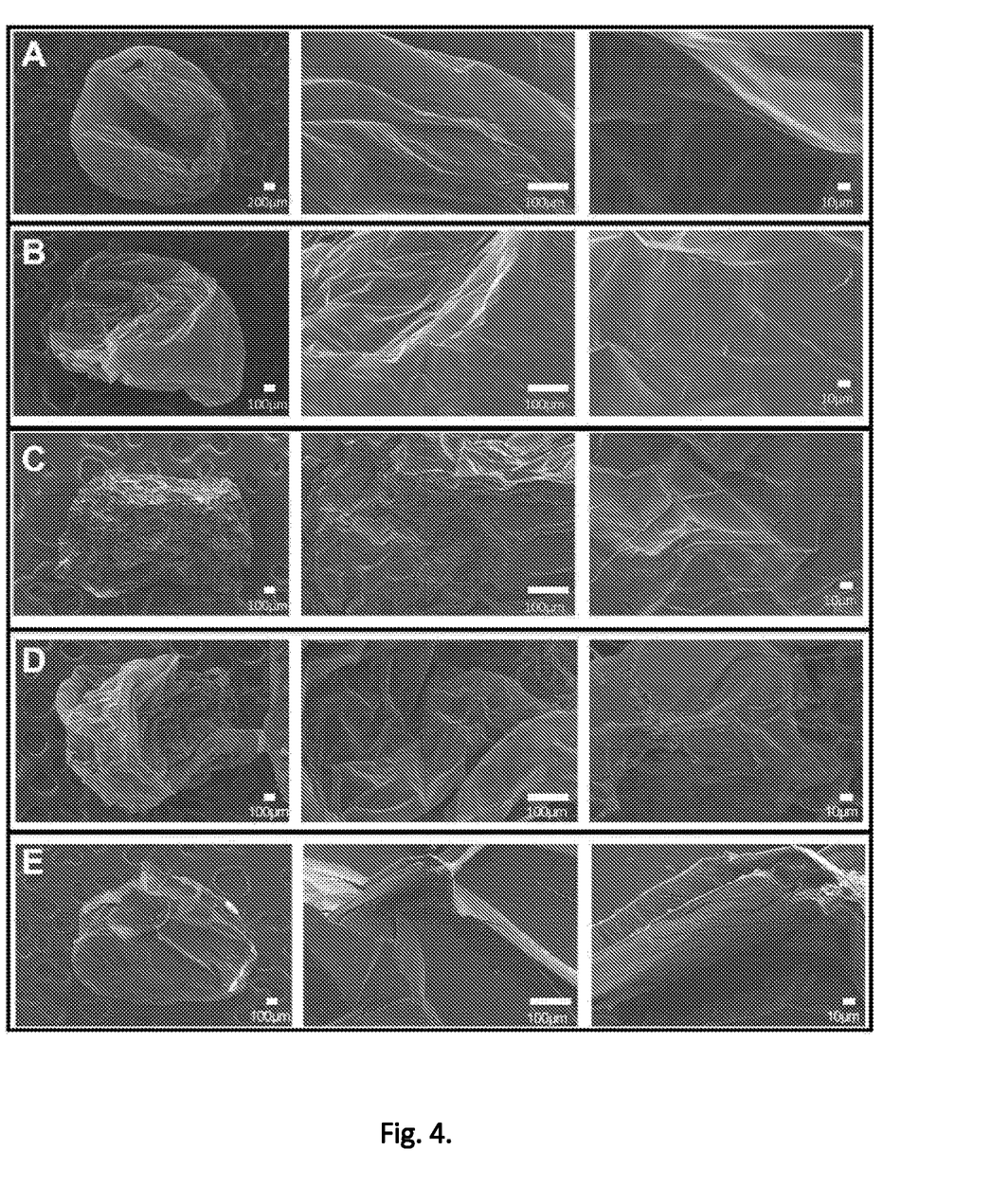
FIG. 4: SEM images of GG/PLL capsules at different magnifications. A—0.5% GG-LA 0.1% PLL after one week in distilled water; B—1% GG-LA 0.1% PLL after one week in distilled water; C—1% GG-LA 0.1% PLL after one week in PBS; D—1% GG-MA 0.1% PLL after one week in distilled water; E—1% GG-MA 0.1% PLL after one week in DMEM.

As it is possible to observe in FIG. 3, when in contact with PBS and DMEM particles size decreases for all conditions. Regarding the presence of water, particles size increases for all conditions except when GG-MA (methacrylated gellan gum) was used. A morphological difference is also noticed when capsules were observed using a magnifying glass (FIG. 3) and SEM (FIG. 4).

The observed shrinkage can be a consequence of ionic crosslinking of inner GG-based polymers, that changes the conformation of gellan. Such modification may cause changes on PEC membrane, including the "crease-like" structures observed.

An embodiment of release studies—The albumin-fluorescein isothiocyanate conjugate (albumin-FITC) was used as a model drug to study the release profile from GG/PLL capsules. Briefly, 1% low acyl gellan gum (GG-LA) solution was heated until 90° C. and then cooled to 37° C. At this point, albumin-FITC (100 µg/mL) was added to the hydrogel and the solution was stirred until complete dissolution, under dark conditions. The mixture was then extruded to a 0.1% (w/v) PLL bath using a 30G needle. The resulted capsules were distributed by three different wells, where each well had three capsules immersed in 1.5 mL of PBS. The release of albumin-FITC was tested at 0.5, 1, 2, 3, 4, 5 and 6 hours. At each time point, the supernatant was removed and equal volume of fresh PBS was added. The fluorescence intensity of 100 µL supernatant of the removed PBS was read by a microplate reader (excitation wavelength at 485/20 nm and the emission wavelength at 528/20) to quantify the albumin-FITC released. The total amount of albumin-FITC incorporated inside the capsules was estimated through their volume.

Figure 5:
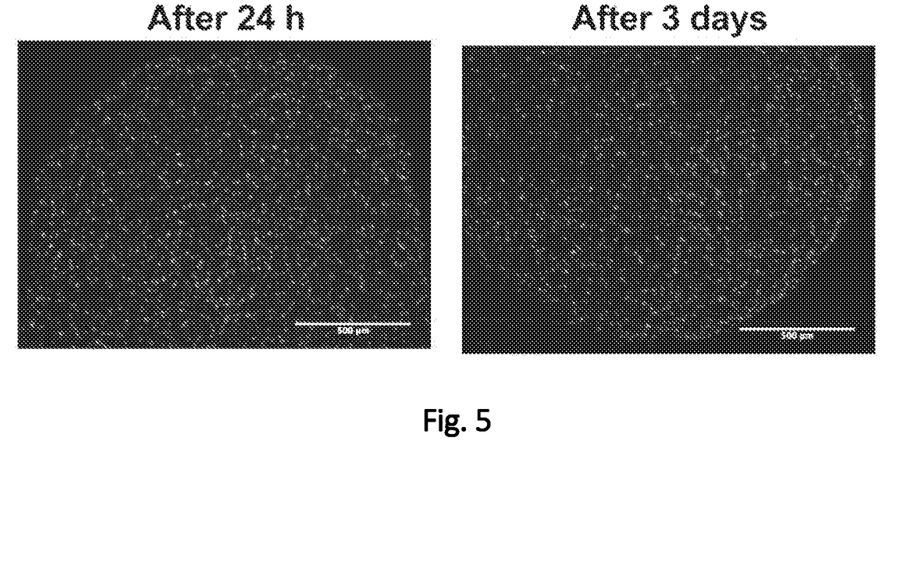
FIG. 5: Live/dead assay on encapsulated androgen-sensitive human prostate adenocarcinoma (LNCaP) cells after 24 hours and 3 days (from left to right).

As depicted in FIG. 5, during the experiment albumin-FITC was slowly released from de capsules. At last, almost 50% of the albumin present in each well was released.

Live Dead Assay—In an embodiment to evaluate the biocompatibility of GG/PLL capsules, androgen-sensitive human prostate adenocarcinoma cells (LNCaP) cells were mixed with 1% GG-MA, and then extruded to a 0.1% PLL solution. After corn plexation, particles were washed with PBS and then cultured for three days in RPMI 1640 media, supplemented with 10% FBS and 1% antibiotic/antimycotic.

As depicted in FIG. 5, the material did not significantly affect cell viability through the three days of experiment. It is also possible to observe a uniform cell distribution within the capsule.

The present disclosure also describes a biomaterial to encapsulate pancreatic islet cells for type I diabetes treatment. The chemical structure of gellan gum (GG), based on a linear anionic heteropolysaccharide, and was exploited to encapsulate cells through its bio-adhesive and thermo-reversible gel properties. Methacrylate, and low acyl forms of GG were studied to obtain gels with different mechanical properties and permeability to biomacromolecules.

At the end, the microcapsule should be able to fully protect the encapsulated cells from the host immune system while allowing the free diffusion of small molecules such as nutrients and oxygen.

Figure 6:
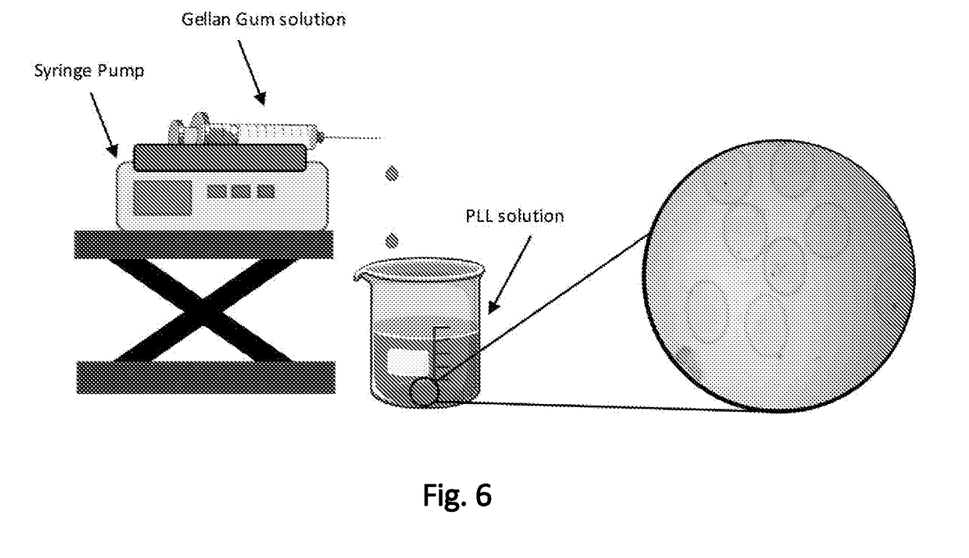
FIG. 6: Schematic representation of GG-PLL spheres, and method of obtaining thereof.

In an embodiment, capsules were formed by gravitational dripping, as illustrated in FIG. 6. Drops with different GG concentrations (0.5, 1 and 1.5% w/v of low acyl GG; 1 and 1.5% GG methacrylate (GG-MA)) were extruded from a 30G syringe into a Poly-L-lysine bath (PLL) with two different concentrations: 0.1 and 0.05% (w/v). This results in the formation of spheres due to the interaction between free carboxylic groups of the GG and the PLL amines, forming polyelectrolyte complexes (PEC). Among the tested conditions, 1% w/v GG-MA with 0.1% PLL was the most reproducible and easy to manipulate. Therefore, the following experiments were performed using this condition.

Figure 8:
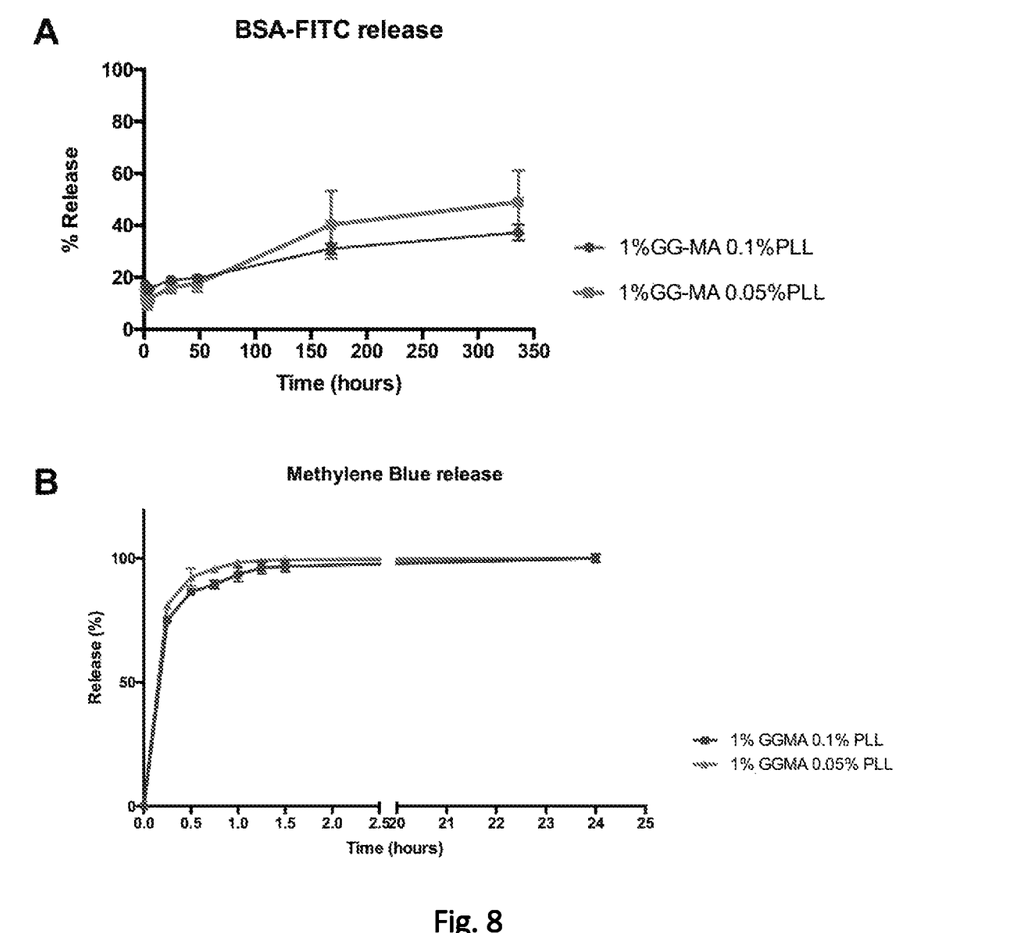
FIG. 8:—Schematic representation of a controlled release of BSA-FITC or Methylene Blue from two different formulations, 1% GG-MA 0.1% PLL capsules and 1% GG-MA 0.05% PLL capsules.

In an embodiment morphology of GG microcapsules of the present disclosure, was assessed using both scanning electron microscopy (SEM) and micrographs (FIG. 8A).

Figure 7A:
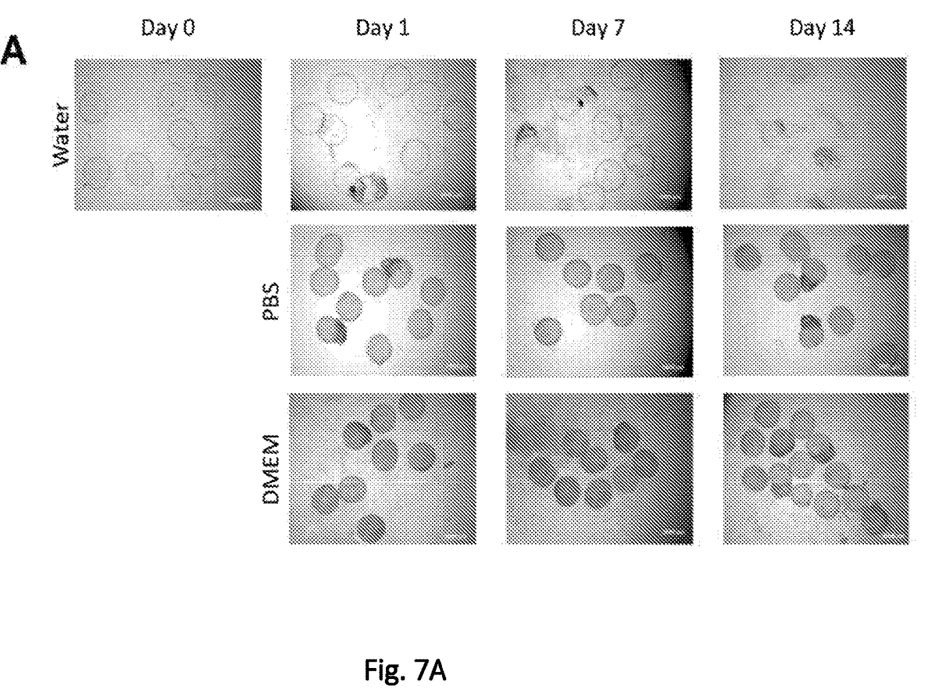
FIG. 7: Characterization of an embodiment of GG microcapsules of the present disclosure, specifically 1% GG-MA 0.1% PLL. A—Micrographs of 1% GG-MA 0.1% PLL capsules immersed in water, PBS or DMEM at 37° C. throughout 14 days; B—SEM images of different magnification of 1% GG-MA 0.1% PLL capsules after 14 days of incubation in PBS (left) or DMEM (right); C—Size of 1% GG-MA 0.1% PLL capsules along the 14 days of incubation. In water, capsules were disrupted after 14 days hampering their measuring; D—Size variation of 1% GG-MA 0.1% PLL capsules as compared to initial capsules (before incubation).
Figure 7B:
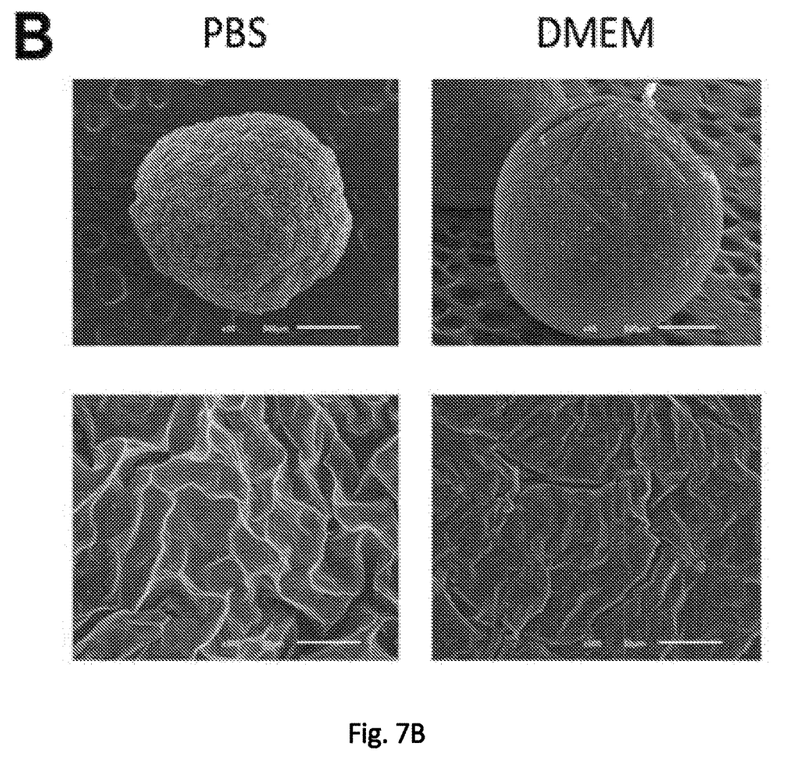
Figure 7C:
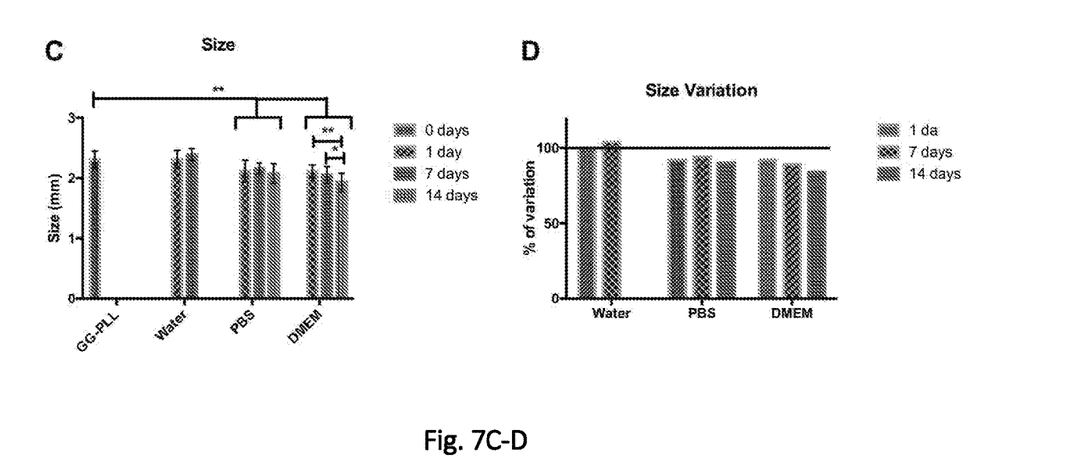

In an embodiment, the diameter of the spheres—GG microcapsules of the present disclosure was, on average, 2.3±0.145 mm after production (FIG. 7C). Then, particles were incubated in water, PBS and DMEM for 14 days at 37° C. to assess the effect of each solution on capsule's size. After the incubation time, it was possible to observe a decrease on spheres diameter of 11% and 14% on capsules incubated respectively with PBS and DMEM (FIG. 7D). This can be due to the diffusion of ions, present in PBS and DMEM, into the capsules, leading to GG gelation. Furthermore, it was possible to observe the formation of a creases on the surface of these capsules that may result from the tightening of the GG chains as result of the ionic cross-linking. SEM images confirm the presence of the crease-like structures only on the surface of capsules incubated with PBS and DMEM.

In an embodiment, the drug release ability of the PEC capsules was assessed using two model molecules. BSA-FITC, with a molecular weight of approximately 66 kDa, was used as a model of large molecules while Methylene Blue, with a molecular weight of 319.85 Da, was used as a small molecule model.

Both compounds were mixed with the GG solutions before the dripping process. After processing, capsules were incubated in PBS at 37° C. Solutions with defined concentrations of BSA-FITC and Methylene Blue were also incubated under the same conditions of the samples, to be used as controls. Furthermore, nine as-prepared capsules were randomly separated into three different eppendorfs, and stored at 4° C. with PBS, to be analysed as t=0 h samples. At each time point, a sample of the supernatant was retrieved and the same volume of fresh PBS was added.

Figure 9:
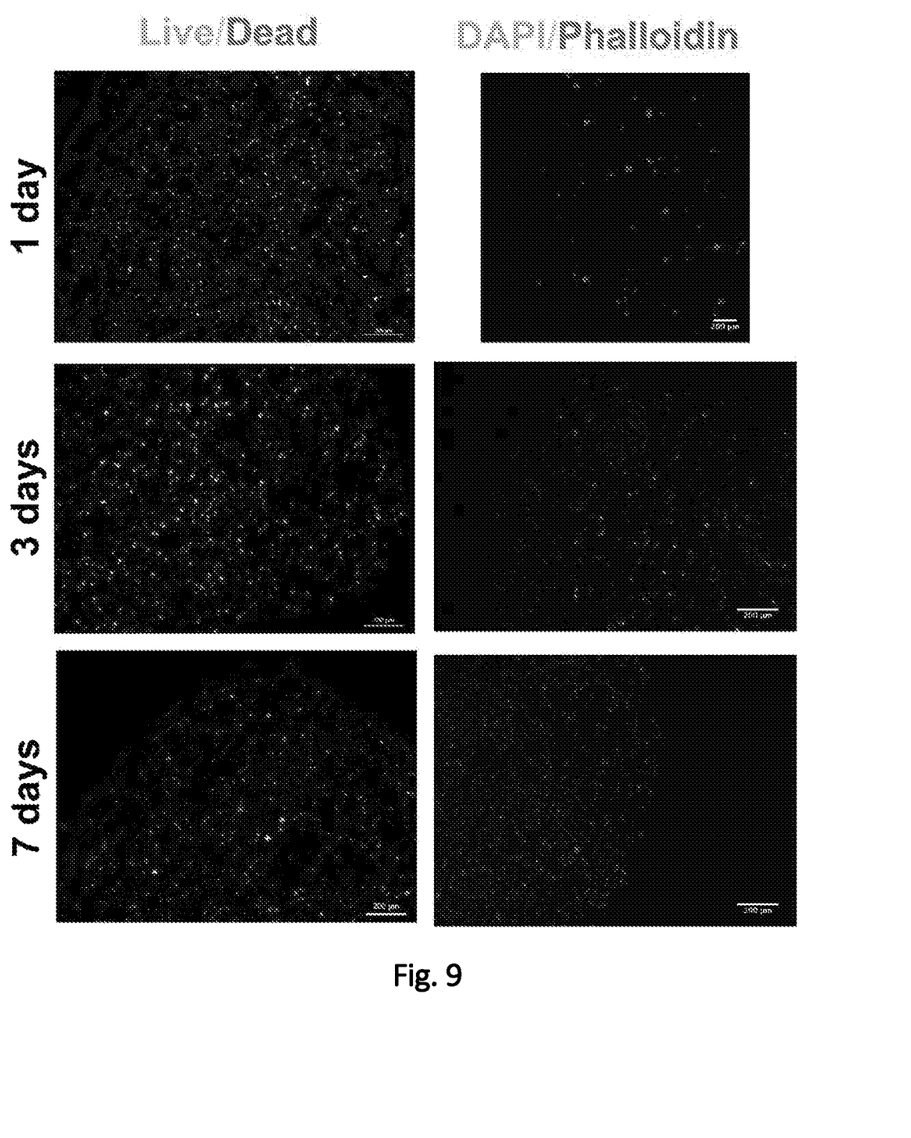
FIG. 9—Pictures confirming that live cells are found inside the PEC capsules of the present disclosure. Live/dead assay and cytoskeleton analysis by DAPI/Phalloidin staining on human adipose derived stem cells.

The results, presented in FIG. 8, have shown a controlled release of BSA-FITC (FIG. 8A). Moreover, it was possible to tune capsules' permeability by changing the concentration of PLL. For 0.1% PLL (w/v), capsules have released 37% of the incorporated BSA-FITC while capsules produced using 0.05% PLL (w/v) released 49% of their content. On the other hand, Methylene Blue was rapidly release from the capsules, with all the material being released within 1 h (FIG. 9B). These results show that PEC capsules have a selective permeability that can be useful for several TE applications.

In an embodiment at last, biocompatibility was also evaluated using human adipose stem cells (hASC). For that, cells were properly mixed in GG-MA solution solutions, at a concentration of $1 \times 10^6$ cell/mL, and microparticles were produced as stated before. Then, cell viability was studied using a Live/Dead staining, followed by fluorescent microscope observation, after defined timepoints.

As depicted in FIG. 9, live cells were found inside the PEC capsules after the experimental timeframe.

The results herein presented show the effect of GG-MA and PLL particles disclosed in the present subject-matter for cell encapsulation strategies. These capsules are easy to produce, using one-step only instead of the commonly used alginate-PLL-alginate system. The spheres are stable on culture media (DMEM) and PBS for at least 14 days and are compatible with hASC, since live cells were found after 7 days of culture.

All references recited in this document are incorporated herein in their entirety by reference, as if each and every reference had been incorporated by reference individually.

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

The above described embodiments are combinable.

The disclosure should not be seen in any way restricted to the embodiments described and a person with ordinary skill in the art will foresee many possibilities to modifications thereof.

The following claims further set out particular embodiments of the disclosure.

The invention claimed is:

1. A spherical capsule composition comprising gellan gum and poly-L-lysine for use in veterinary or in human medicine, wherein the composition comprises:
   0.05-0.1% (w/v) of poly-L-lysine, and
   0.5-3% (w/v) of a methacrylated gellan gum.

2. The composition according to claim 1 wherein the methacrylated gellan gum comprises a methacrylation degree up to 10%.

3. The composition according to claim 2, wherein the methacrylation degree is between 1-2%.

4. The composition according to claim 1 wherein the methacrylated gellan gum molecular weight is between $5 \times 10^4$ Da to $2 \times 10^6$ Da.

5. The composition according to claim 1 wherein the poly-L-lysine molecular weight is between 30-500 kDa.

6. The composition according to claim 1 further comprising at least a second hydrogel or more hydrogel.

7. The composition according to claim 6 wherein the second, or more hydrogels, is selected from a list consisting of carbopol, hyaluronic acid, carboxymethylchitosan, dextran, alginate, collagen, and mixtures thereof.

8. The composition according to claim 1 further comprising a coupling agent.

9. The composition according to claim 8 wherein said coupling agent is selected from the group consisting of 4-(4,6-dimethoxy-1,3,5-triazin-2-yl)-4-methylmorpholinium chloride, glutaraldehyde, epichlorohydrin, dianhydrides, diamines, and mixtures thereof.

10. A composition according to claim 1 for use in the treatment or prevention of diseases that involve the repair or regeneration of tissues.

11. A composition according to claim 1 for use as a drug delivery system.

12. The composition according to claim 1 for use in cell therapy or advanced-therapy medicinal product.

13. The composition according to claim 1 for use in the treatment or prevention of diabetes, obesity, ageing related-diseases, tumours or pancreatic diseases.

14. The composition according to claim 1 for use in the treatment or prevention of pancreatic cancer.

15. The composition according to claim 1 for the treatment or prevention of female infertility.

16. The composition according to claim 1 further comprising an anti-inflammatory agent, an antiseptic agent, an antipyretic agent, an anaesthetic agent, a therapeutic agent, a biological cell, a biological tissue and combinations thereof.

17. The composition according to claim 16 comprising an animal or human cell, or stem cell, or combinations thereof.

18. The composition according to claim 17 comprising an animal or human pancreatic β-cell or androgen-sensitive human prostate adenocarcinoma cell.

19. The composition according to claim 16 comprising human tissue.

* * * * *